United States Patent
Florio et al.

(10) Patent No.: US 7,056,314 B1
(45) Date of Patent: Jun. 6, 2006

(54) STEERABLE OBTURATOR

(75) Inventors: Joseph J. Florio, La Canada, CA (US); Gene A. Bornzin, Simi Valley, CA (US); Kevin L. Morgan, Simi Valley, CA (US); Sheldon Williams, Green Valley, CA (US); Janice Barstad, Eden Prairie, MN (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 10/452,244

(22) Filed: May 30, 2003

(51) Int. Cl.
*A61M 25/01* (2006.01)

(52) U.S. Cl. .................................. 604/528; 604/95.01

(58) Field of Classification Search ............... 604/523, 604/95.01, 528, 164.13, 164.01; 600/459–463, 600/446, 439
See application file for complete search history.

(56) References Cited

U.S. PATENT DOCUMENTS

| | | | | |
|---|---|---|---|---|
| 4,815,478 A | 3/1989 | Buchbinder et al. | ........ | 128/772 |
| 5,403,297 A | * 4/1995 | Imran | .......................... | 604/531 |
| 5,545,200 A | 8/1996 | West et al. | .................. | 607/122 |
| 5,599,305 A | * 2/1997 | Hermann et al. | ......... | 604/95.04 |
| 5,656,030 A | 8/1997 | Hunjan et al. | ................. | 604/95 |
| 5,785,706 A | 7/1998 | Bednarek | ...................... | 606/41 |
| 5,873,842 A | 2/1999 | Brennen et al. | ............. | 600/585 |
| 5,935,102 A | 8/1999 | Bowden et al. | ................ | 604/95 |
| 5,938,616 A | * 8/1999 | Eaton et al. | .................. | 600/463 |
| 6,113,556 A | 9/2000 | Avitall | ......................... | 600/585 |
| 6,123,699 A | 9/2000 | Webster, Jr. | ................. | 604/528 |
| 6,132,390 A | 10/2000 | Cookston et al. | ............ | 600/585 |
| 6,144,882 A | 11/2000 | Sommer et al. | ............. | 607/125 |
| 6,146,338 A | 11/2000 | Gardeski et al. | ............. | 600/585 |
| 6,198,974 B1 | 3/2001 | Webster, Jr. | ................. | 607/122 |
| 2001/0044624 A1 | 11/2001 | Seraj et al. | .................... | 607/41 |

FOREIGN PATENT DOCUMENTS

WO   WO 01/64279 A1   9/2001
WO   WO 01/72368 A2   10/2001

* cited by examiner

*Primary Examiner*—Kevin C. Sirmons

(57) ABSTRACT

An omnidirectionally steerable obturator facilitates the delivery of the distal tip of an introducer sheath into the coronary sinus of a heart. The steerable obturator comprises an obturator body extending longitudinally along a central axis, the obturator body being configured to be received by the introducer sheath. The obturator body further has a flexible, deflectable distal end section terminating in a rounded distal tip. An actuator, controllable from a proximal end of the obturator body, is operatively associated with the flexible distal end section of the obturator body to cause deflection of the flexible distal end section of the obturator body in at least one selected direction to facilitate passage of the distal end section of the obturator body and the distal tip of the introducer sheath into the coronary sinus of the heart.

The obturator body is preferably configured to be received in a close fit within at least the tip of the introducer sheath. More preferably, the distal end of the obturator body has an outer surface and the fit between the outer surface of the obturator and at least the tip of the introducer sheath comprises substantially a line-to-line fit.

18 Claims, 13 Drawing Sheets

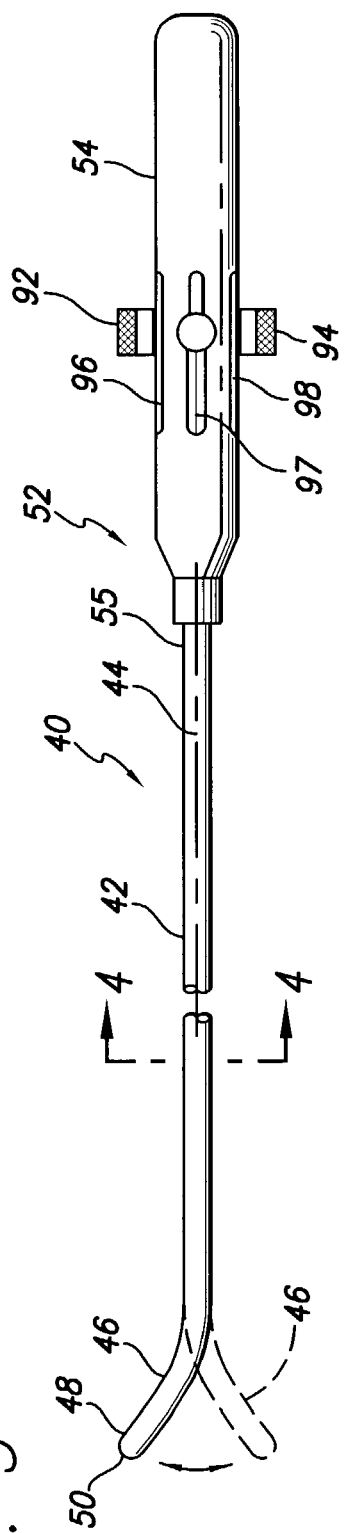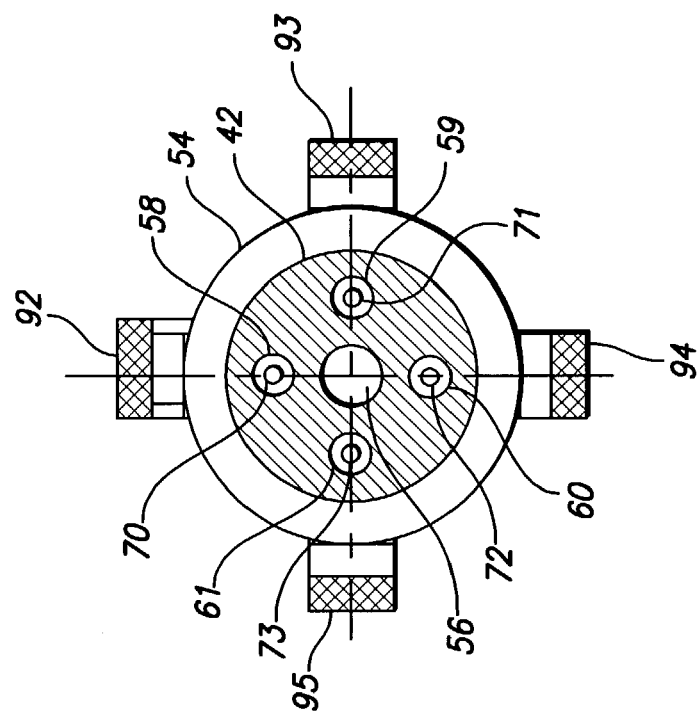

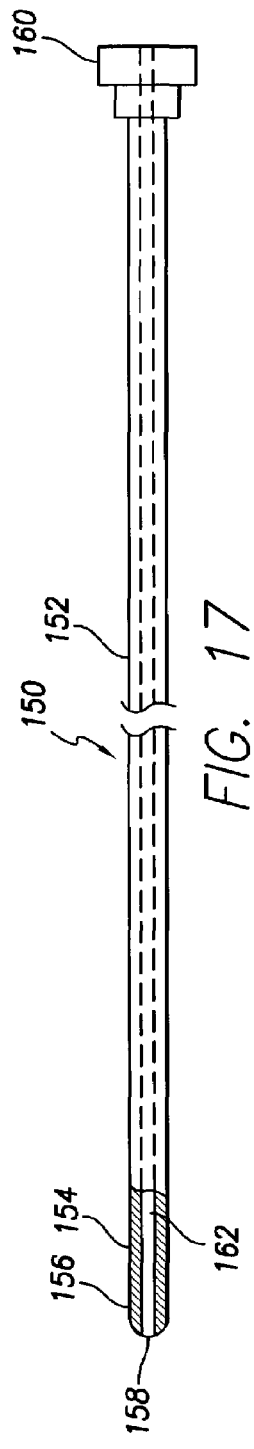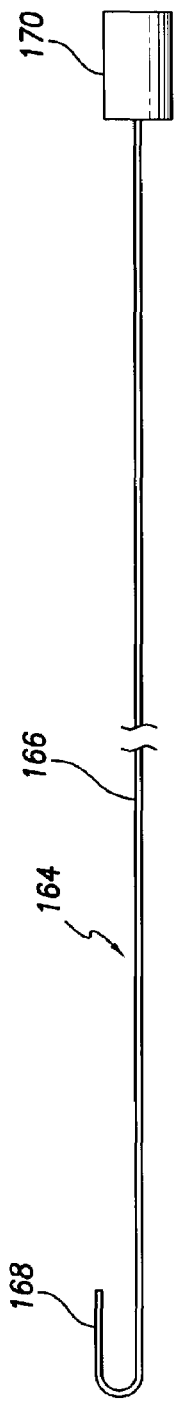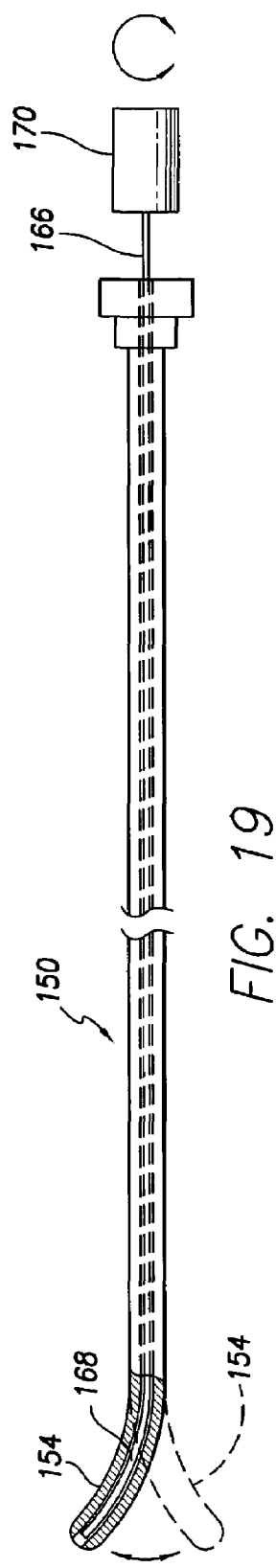

STEERABLE OBTURATOR

FIELD OF THE INVENTION

The present invention relates generally to body implantable leads. More particularly, the invention relates to a steerable obturator or cannulator for facilitating the delivery of an introducer sheath and a body implantable lead into the coronary sinus region of the heart.

BACKGROUND OF THE INVENTION

The advantages of providing pacing therapies to both the right and left heart chambers are well established. For example, in four chamber pacing systems, four pacing leads, typically bipolar leads, are positioned for both pacing and sensing in the respective heart chambers. To provide left side stimulation and sensing, leads are transvenously implanted in the coronary sinus region, for example, in a vein such as the great cardiac vein or the left posterior ventricular (LPV) vein proximate the left ventricle of the heart, or any other vein deemed suitable. Such placement avoids the risks associated with implanting a lead directly within the left ventricle which can increase the potential for the formation of blood clots which may become dislodged and then carried to the brain where even a small embolism could cause a stroke. As used herein, the phrase "coronary sinus region" refers to the coronary sinus, great cardiac vein, left marginal vein, left posterior ventricular vein, middle cardiac vein, and/or small cardiac vein or any other vein accessible by way of the coronary sinus. The coronary sinus drains into the right atrium through the coronary sinus ostium or os.

The tip electrode of a lead implanted in the coronary sinus region can pace and sense left side ventricular activity. When such a lead includes a second electrode proximal of the tip electrode and residing in the coronary sinus above the left ventricle closely adjacent to the left atrium of the heart, pacing and sensing of left atrial activity is made possible. Moreover, the lead may include one or more electrodes for the delivery of electrical shocks for terminating tachycardia and/or fibrillation. Such cardioverting/defibrillating electrodes may be used by themselves or may be combined with pacing and/or sensing electrodes.

The implantation of a lead in the coronary sinus region is often difficult because of the extreme curvatures in the coronary vessels, their narrowness, anomalies in the vascular anatomy because of disease, and the number of veins which may communicate with the desired lead placement path. To facilitate placement of a lead in the coronary sinus region, an introducer sheath and dilator, often in combination with a stylet and/or guide wire, are conventionally used.

FIG. 1 is a side view of an introducer sheath 10. The introducer sheath has a main body 12 having a distal, tapering end 14 and a proximal end carrying a handle 16. The introducer sheath has a central passage 18 extending the entire length of the sheath. The passage 18 allows various objects, such as a dilator or a guide wire, to be inserted through the sheath. The introducer sheath has a length ranging, for example, from about 35 cm to about 70 cm, so that the distal end 14 of the introducer reaches the coronary sinus os. The introducer may further be configured to curve past the coronary sinus os either by constructing the distal end of the introducer to be flexible enough for a pre-curved guide wire to guide the introducer into the coronary sinus os or by pre-shaping the distal end of the introducer.

The tapered distal end 14 is substantially conical in shape converging to a circular edge 20 at the distal extremity. The introducer sheath may be made of any biostable, biocompatible material such as polyethylene and may comprise a peel-away structure of the kind well known in the art.

FIG. 2 is a side view of the introducer sheath 10 showing a dilator 30 fully inserted therein. The dilator 30 is typically a tubular member comprising a tapered distal end 32 and a knob 34 attached to the proximal end. Typically, the dilator will be somewhat stiffer than the introducer sheath. The dilator may have a length in the range of about 40–90 cm. The tapered distal end 32 of the dilator terminates at a point 36. The knob 34 at the proximal end of the dilator allows a clinician to manipulate the dilator during its insertion into or removal from the introducer sheath.

When inserted into the introducer sheath 10, the dilator 30 provides increased stiffness to the introducer sheath during introduction or insertion into tissue. The tip 36 of the tapered end of the dilator allows for easy entry through the skin into the subclavian or cephalic vein. By advancing the knob 34 relative to the introducer handle 16 and into engagement therewith, the dilator may be fully inserted into the introducer sheath. When fully inserted inside the introducer sheath, a length of about 1–10 cm of the dilator remains extended through and out of the distal end of the introducer sheath.

A typical, presently used method of implanting a lead using the introducer sheath and dilator is as follows:

Following standard Seldinger technique, an 18-gauge needle (not shown) is inserted into a vein (subclavian or cephalic). A J-tipped guide wire (not shown) is placed into the needle and advanced into the vein through the needle. The needle is then removed over the guide wire. The dilator, while located within the introducer, is pushed over the J-tipped guide wire through the tissue and ultimately into the vein and finally into the superior vena cava (SVC). At this point, the dilator and the J-tipped guide wire are pulled out of the introducer. The open end of the introducer is then placed in the right atrium near the coronary sinus os and the sheath is maneuvered as necessary to pass the tapered end thereof through the os. Once the introducer sheath is in place, a guide wire is inserted into the introducer sheath and advanced until the guide wire is inside the coronary sinus. The guide wire may be further advanced and maneuvered within the coronary sinus until the guide wire reaches a target vessel such as the LPV vein. The lead is then slid over the guide wire and advanced inside the introducer sheath until the distal end portion of the lead is inside the coronary sinus. While keeping the guide wire in the desired location (e.g., the LPV vein), the lead is further advanced along the guide wire for placement of the distal end portion thereof in the LPV vein. After placement of the lead, the guide wire is withdrawn from the lead followed by the removal of the introducer sheath. Alternatively, the lead may be placed using a stylet without a guide wire.

The introducer sheath is directed through the coronary sinus os with the aid of a fluoroscope. Nevertheless, the location of the coronary sinus os is difficult to ascertain and steering the introducer through the coronary sinus os is a difficult maneuver much dependent upon operator skill.

Obturators inserted within an introducer sheath have been used to facilitate passage of the introducer through the coronary sinus os. However, in current systems designed to deliver leads into the coronary sinus the distal portion of the obturator is pre-curved and accordingly its shape is thereby fixed. In many instances this does not provide adequate control to cannulate the coronary sinus. Further, because a substantial clearance typically exists between the outer surface of the distal portion of the obturator and the central passage of the introducer sheath, the edge of the tapered distal end of the sheath (such as the edge 20 in FIG. 1) may be disposed to engage cardiac tissue as the distal end of the introducer sheath is maneuvered into the coronary sinus.

SUMMARY

In accordance with one specific, exemplary embodiment, there is provided an omnidirectionally steerable obturator for facilitating the delivery of the distal tip of an introducer sheath into the coronary sinus of a heart. The steerable obturator comprises an obturator body extending longitudinally along a central axis, the obturator body being configured to be received by the introducer sheath. The obturator body further has a flexible, deflectable distal end section terminating in a rounded distal tip. An actuator, controllable from a proximal end of the obturator body, is operatively associated with the flexible distal end section of the obturator body to cause deflection of the flexible distal end section of the obturator body in at least one selected direction to facilitate passage of the distal end section of the obturator body and the distal tip of the introducer sheath into the coronary sinus of the heart.

In accordance with another aspect of the invention, the obturator body is configured to be received in a close fit within at least the tip of the introducer sheath so that the distal edge of the introducer sheath lies against the outer surface of the obturator body's distal end section so as to minimize protrusion of the distal edge of the sheath and present to the body tissue a substantially smooth, continuous surface. Accordingly, the distal edge of the sheath is not disposed to engage cardiac tissue as the sheath is maneuvered into the coronary sinus. More specifically, the distal end of the obturator body has an outer surface and the fit between the outer surface of the obturator and at least the tip of the introducer sheath preferably comprises substantially a line-to-line fit.

Pursuant to another aspect of the invention, the actuator comprises a control handle attached to the proximal end of the obturator body and at least one elongated actuating member coupling the control handle to the flexible distal end section of the obturator body. The obturator body further includes a plurality of parallel, longitudinally extending, off-axis lumens, the control handle includes a plurality of manually movable control members, and an elongated actuating member is contained within each off-axis lumen. Each actuating member has a distal end anchored to an interior surface of the distal end section at an off-axis point and a proximal end coupled to one of the movable control members on the control handle. Movement of one or more selected control members causes deflection of the flexible distal end section of the obturator body.

In accordance with another specific, exemplary embodiment of the invention, the actuator comprises a stylet adapted to be received within a longitudinally-extending lumen formed in the obturator body, the stylet having a pre-curved, preferably generally J-shaped, flexible distal tip section. The pre-curved distal tip section of the stylet deflects the distal end section of the obturator body so as to provide steerability thereof. Rotation of the stylet within the obturator body determines the direction of the deflection of the distal end section of the obturator body as required to cannulate the coronary sinus.

BRIEF DESCRIPTION OF THE DRAWINGS

The foregoing and other objects, features and advantages of the invention will be evident to those skilled in the art from the detailed description of the invention, below, taken together with the accompanying drawings, in which:

FIG. 3 is a side view of a steerable obturator in accordance with a first embodiment of the present invention;

FIG. 4 is a sectional view of the obturator of FIG. 3 as seen along the line 4—4 in FIG. 3;

FIG. 17 is a side view, partly in section, of an obturator in accordance with yet another exemplary embodiment of the present invention;

FIG. 18 is a side view of a pre-bent stylet used with the obturator of FIG. 17; and FIG. 19 is a side view, partly in section, of the obturator of FIG. 17 with the pre-bent stylet inserted within the obturator.

DETAILED DESCRIPTION OF THE INVENTION

Figure 1:
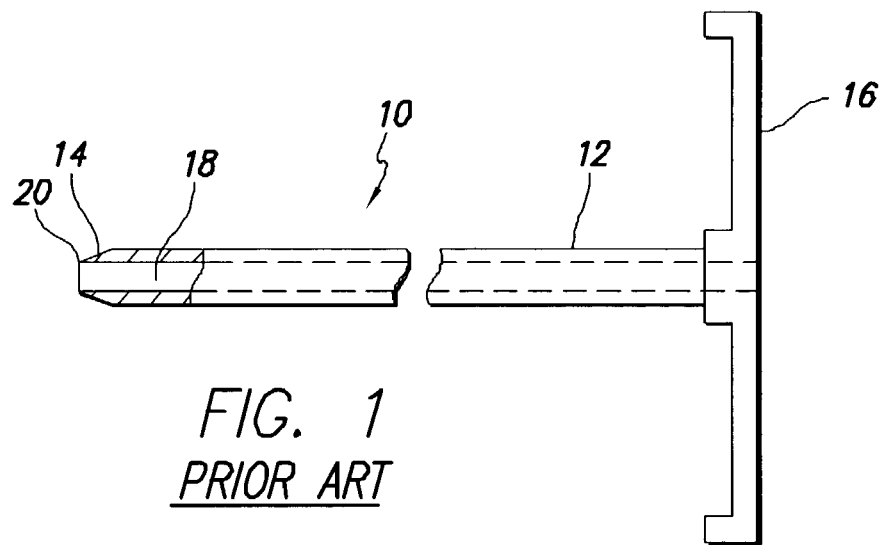
FIG. 1 is a side view of a typical introducer sheath presently used for delivering a lead into the coronary sinus region of the heart.
Figure 2:
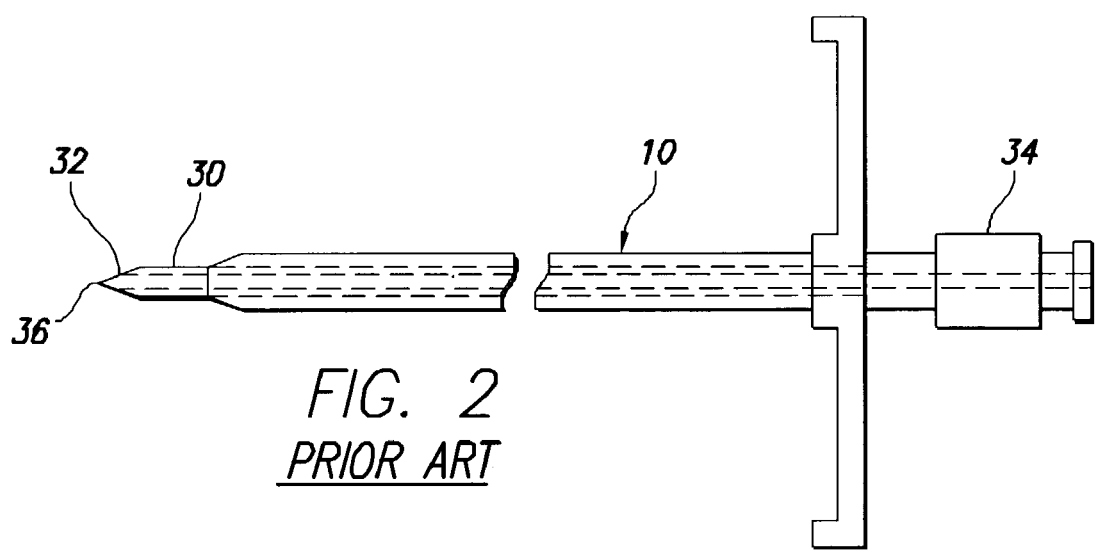
FIG. 2 is a side view of the introducer sheath of FIG. 1 with a dilator substantially fully inserted therein.

The following description presents preferred embodiments of the invention representing the best mode contemplated for practicing the invention. This description is not to be taken in a limiting sense but is made merely for the purpose of describing the general principles of the invention whose scope is defined by the appended claims.

FIGS. 3–8 show a steerable obturator 40 in accordance with a first embodiment of the invention. The obturator 40 comprises an elongated obturator body 42 extending along a longitudinal, central axis 44. The obturator body includes a flexible, omnidirectionally deflectable distal end section 46 terminating at a distal tip 48 having a curved or rounded outer tip surface 50. The distal end section 46 of the obturator body may comprise a short section that is more flexible than the remainder of the obturator body. A directional actuator 52 is provided for deflecting the flexible distal end section 46. In accordance with one embodiment of the invention, the actuator 52 includes a control handle 54 attached to a proximal end 55 of the obturator body 42.

The obturator body 42 comprises a generally tubular structure fabricated of any suitable biostable, biocompatible, flexible material, for example, a braided stainless steel wire embedded in a thermoplastic resin such as that sold under PEBAX®, a trademark for polyether-block co-polyamide polymers. The body 42 defines a central, coaxial longitudinal lumen 56 surrounded by four off-axis or eccentric outer lumens 58–61 which in the specific example shown are arranged symmetrically about the central lumen 56. The central lumen 56 extends the entire length of the obturator 40 between a proximal opening 64 at the proximal extremity of the control handle 54 and a distal opening 66 formed in the distal tip 52. The overall length and diameter of the obturator body 42 may vary according to the application. Preferably, the length of the obturator is such that when fully inserted in an introducer sheath, the obturator's distal end extends at least about 5 cm, and more preferably about 10 cm, beyond the tip of the introducer.

The central lumen 56 of the obturator provides a passageway for a guide wire, or a contrast dye, or an imaging probe such as a fiber optic bundle or an ultrasonic probe, as will be explained in greater detail below.

Figure 5:
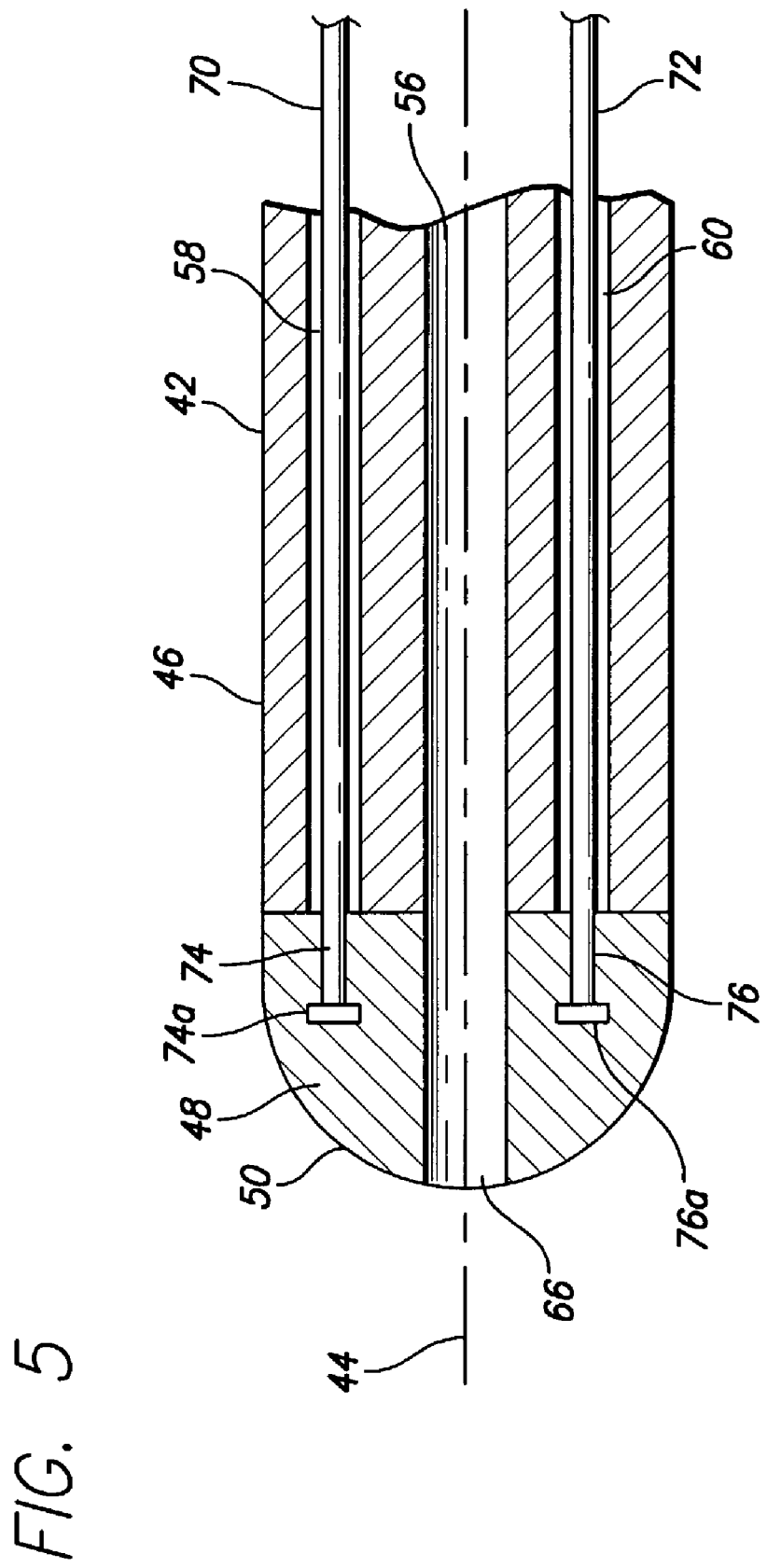
FIG. 5 is an axial, sectional view of a portion of the distal end section of the obturator of FIG. 3.

The actuator 52 further includes elongated actuation members 70–73, which may comprise pull wires or cables, that extend from the control handle 54 through the outer lumens 58–61, respectively, in the obturator body. The members 70–73 have distal extremities such as the extremities 74 and 76 of the members 70 and 72, respectively, anchored at off-axis points 74a and 76a within the tip 48 of the obturator body as best seen in FIG. 5. The actuation members 70–73 may be made of any suitable material comprising, by way of example and not limitation, a metal, a metallic alloy, or a non-metallic material such as a polymer, a carbon composite, KEVLAR®, and so forth. To minimize friction, the members 70–73 may be appropriately surface-treated or coated with a low friction film of TEFLON® or the like.

It will be evident that the locations of the anchor points of the distal extremities of the actuation members 70–73 along the length of the obturator body may be different than those shown in FIG. 5 and that many variations are possible. For example, the distal extremities of one or more of the elongated members may be anchored to the obturator body at off-axis points located proximally of the tip 48. In accordance with one variation, shown in FIG. 6, all of the members 70–73 may be anchored at points lying along a common plane 77 proximal of the tip 48. Alternatively, as suggested by FIG. 6, two of the members (70 and 72) may be anchored along the plane 77 with the remaining two members 71 and 73 (not shown in FIG. 6) anchored proximally or distally of the plane 77. Still further, each of the various actuating members 70–73 may be anchored at a different distance from the tip 48 as illustrated in FIG. 7 in which the member 70 is anchored at a first off-axis point 78 proximally of the tip 48 and the member 72 is anchored at a second off-axis point 79 proximally of the first point 78. It will be appreciated that compound deflections of varying curvatures may thus be formed in the distal end section 46 of the obturator body to enhance the ability to quickly steer the distal end section 46 and the tip of the introducer sheath carried thereby through the coronary sinus os and into the coronary sinus.

Figure 8:
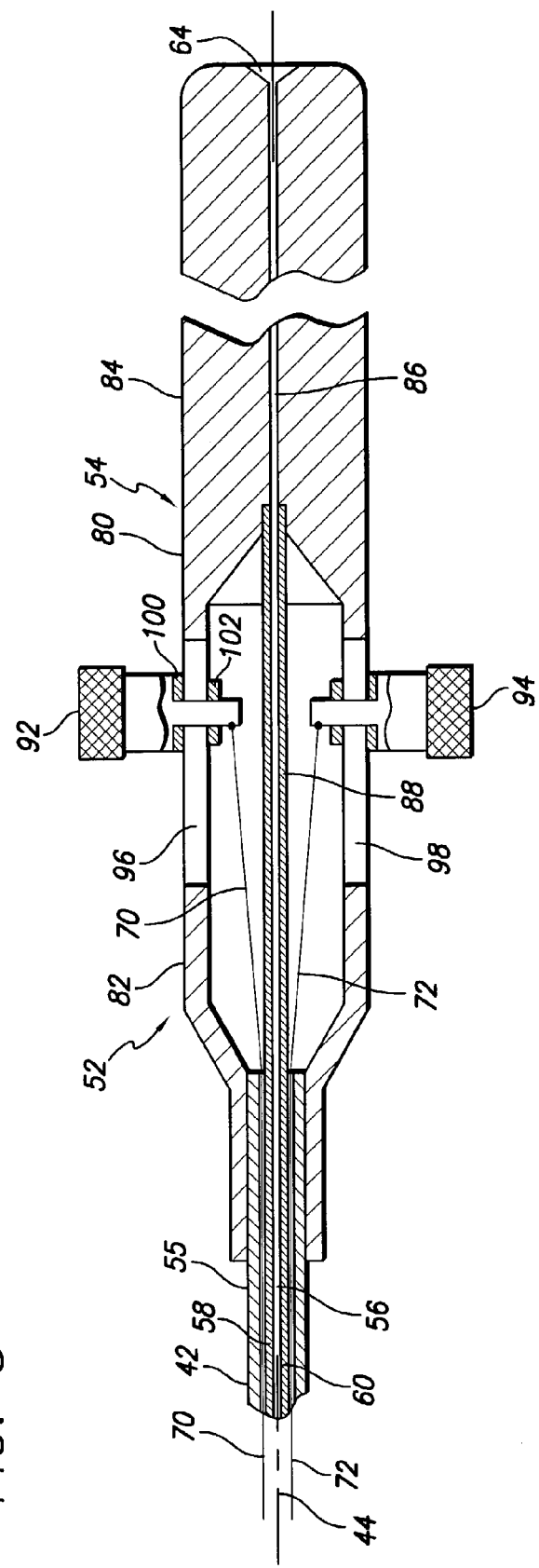
FIG. 8 is a sectional side view of a steering control handle forming part of the obturator of FIG. 3.

Longitudinal movements of the members 70–73 are effected by the control handle 54. As best seen in FIG. 8, the handle 54 comprises a generally cylindrical main body 80 having a distal tubular portion 82 attached to the proximal end 55 of the obturator body and a proximal portion 84 including a central lumen 86 communicating with the central lumen 56 in the obturator body via a tube 88. The actuation members 70–73 are attached at their proximal ends to displacement control members, for example, knobs 92–95, respectively, longitudinally slidable along the length of the tubular portion 82 of the handle 54 within slots 96–98, respectively, formed in the tubular portion. Thus, each knob may be independently advanced or retracted in coordination with the other knobs to appropriately deflect the distal end section 46 of the obturator body to guide and steer the tip of the obturator around obstructions and ultimately into the coronary sinus os. Retraction of a selected one of the knobs 92–95 deflects the distal end section 46 in the direction of the elongated actuating member associated with the selected knob. Frictional elements, such as the elements 100 and 102 cooperating with the knob 92, provide an appropriate level of resistance to movement of the knobs, introducing sufficient friction so that a selected knob is retained in the position in which it is placed. Further, detents (not shown) may can be added to aid such retention.

Figure 6:
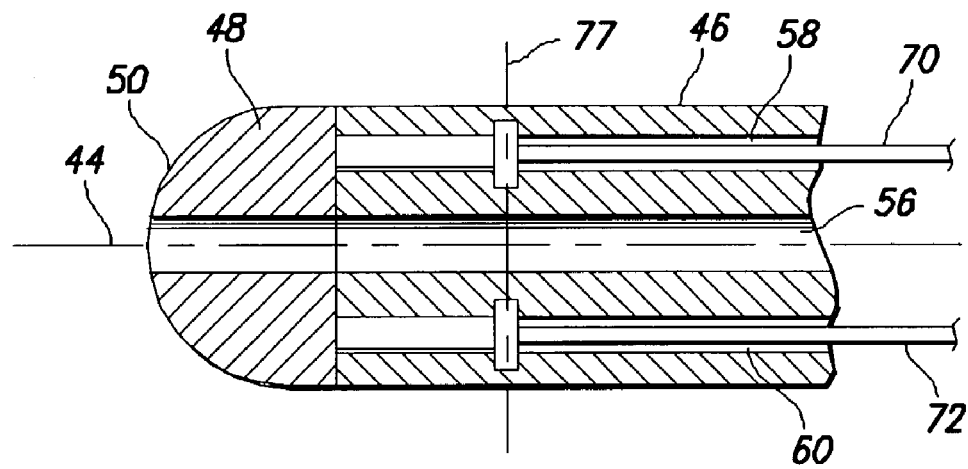
FIG. 6 is an axial sectional view of a portion of the distal end section of the obturator of FIG. 3 in accordance with a variation thereof.
Figure 7:
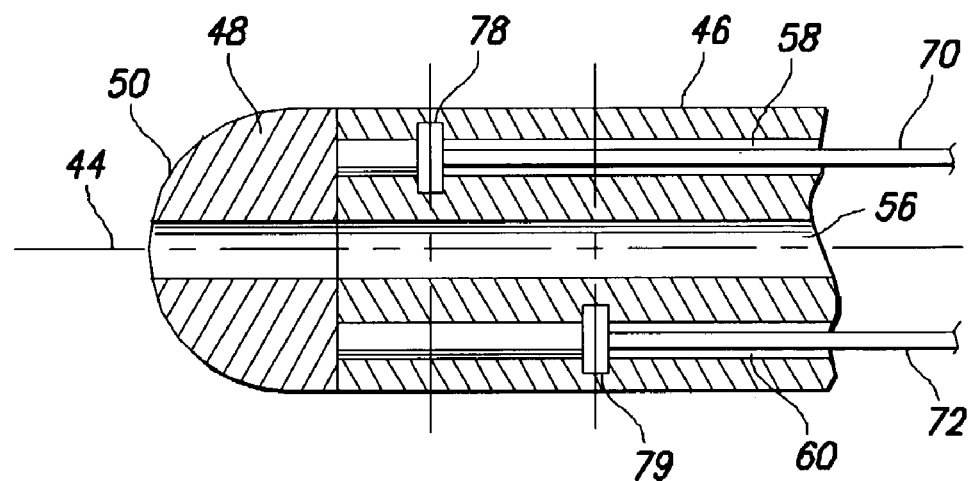
FIG. 7 is an axial sectional view of a portion of the distal end section of the obturator of FIG. 3 in accordance with another variation thereof.

As already noted with reference to FIGS. 5–7, the distal extremities of the actuation members 70–73 may be anchored at off-axis points within the tip 48 of the obturator body. Differential longitudinal displacements of selected ones of the knobs 92–95 along the handle 54 thus control the direction of the deflection of the distal end section 46 as well as the radius of curvature of the deflection.

FIGS. 9–16 show an approach to the delivery of the distal end portion of a stimulation lead to the coronary sinus and the coronary veins accessible by way of the coronary sinus, using an obturator in accordance with the embodiments of FIGS. 3–8.

Figure 9:
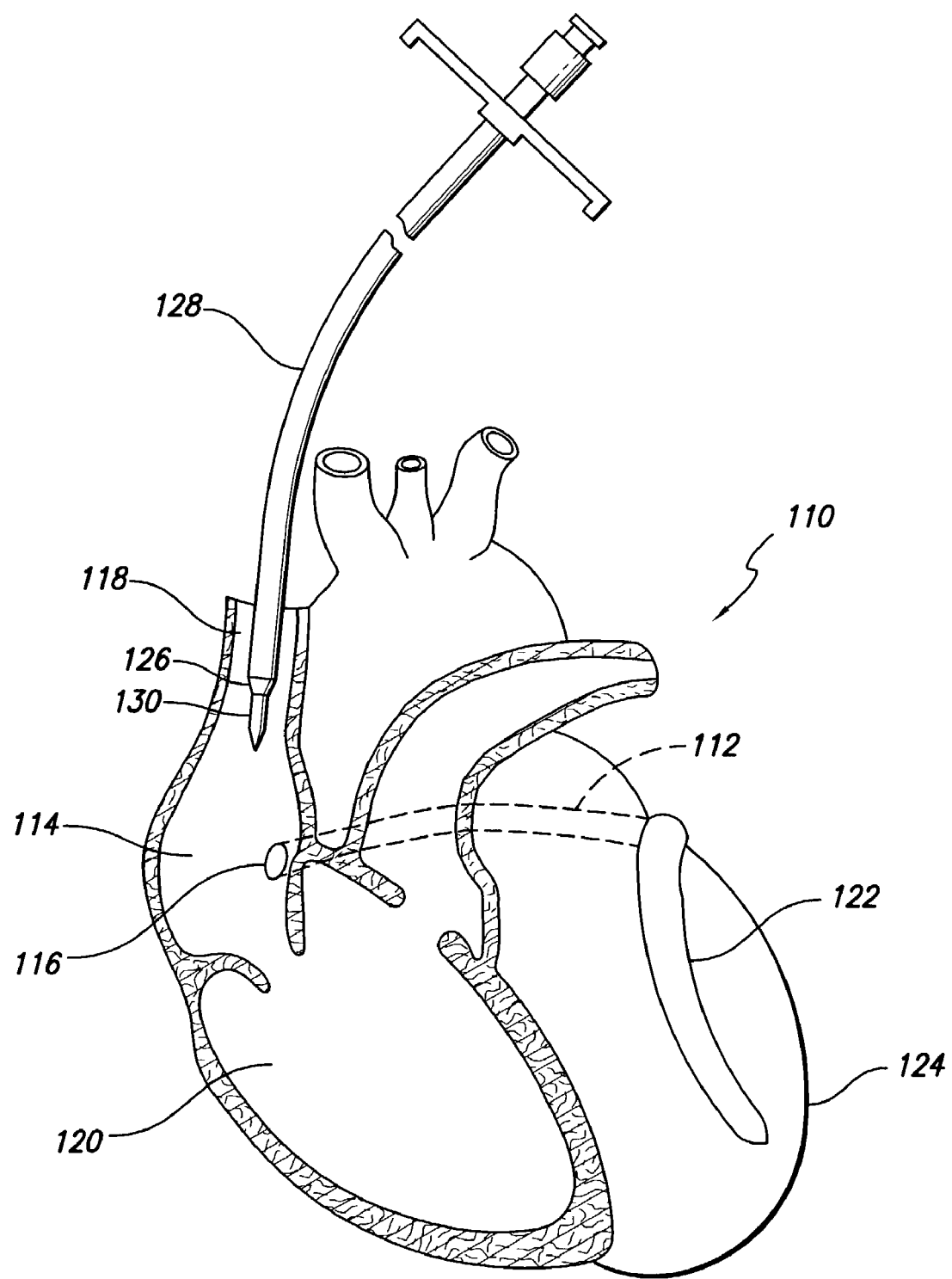
FIG. 9 is a perspective view of the anterior portion of a heart showing an introducer sheath with a dilator fully inserted therein in the right atrium near the coronary sinus os.

FIG. 9 includes a simplified, perspective view of the anterior portion of a heart 110 showing the relevant anatomy thereof. The coronary sinus 112 is the main collecting vein of the heart and drains into the right atrium 114 through the coronary sinus os 116. The right atrium is located intermediate the superior vena cava (SVC) 118 and the right ventricle 120. The coronary sinus 112 connects to various veins overlying the heart, including the posterior vein 122 of the left ventricle 124 usually referred to as the left posterior ventricle (LPV) vein. In the example under consideration, the distal end portion of a stimulation lead is to be placed inside the LPV vein 122 for pacing, sensing, and/or cardioversion/defibrillation of the left ventricle 124.

Figure 10:
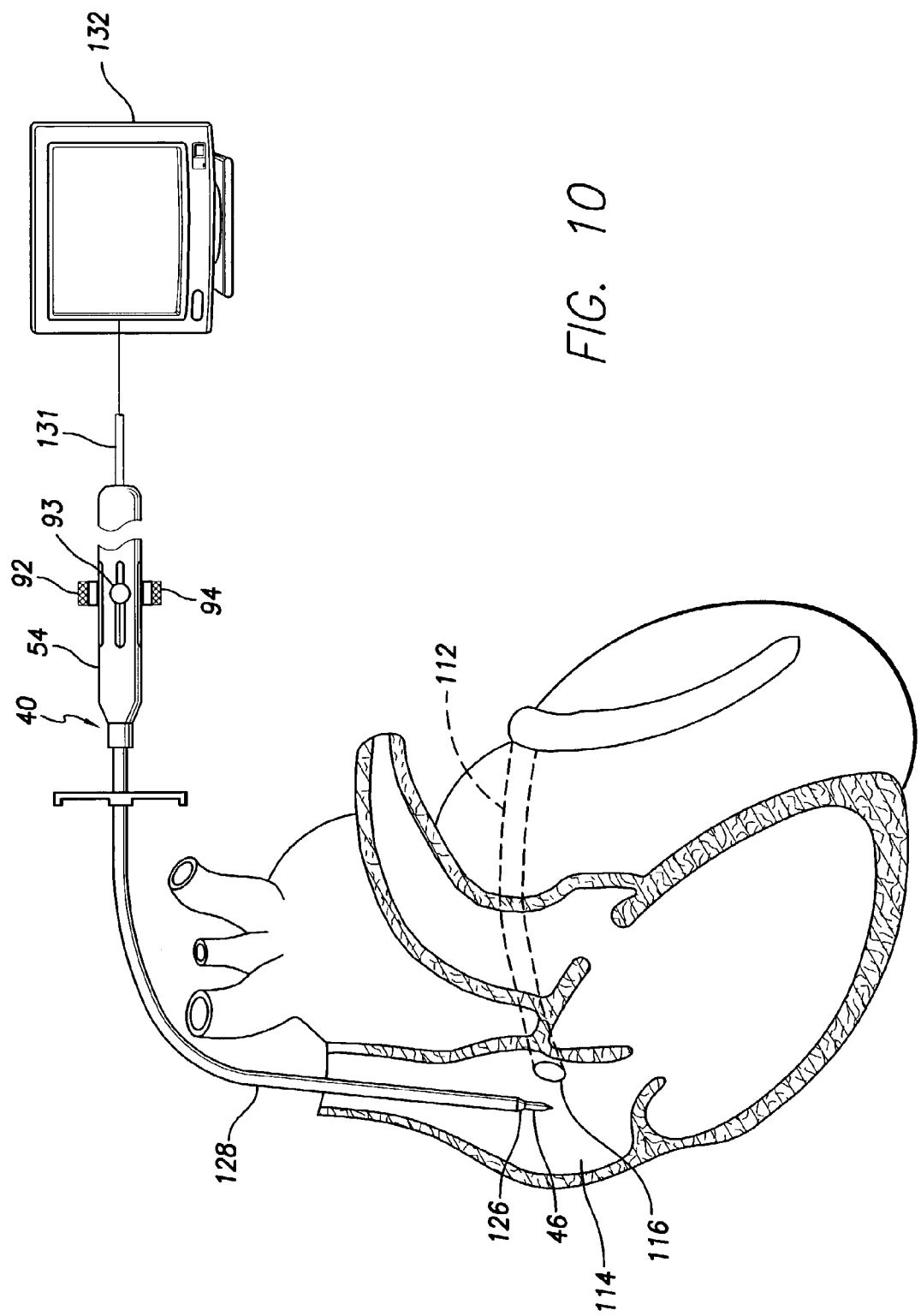
FIG. 10 is a perspective view of the anterior portion of the heart showing the introducer sheath with the distal tip thereof in the right atrium near the coronary sinus os after the dilator has been withdrawn from the introducer sheath and a steerable obturator in accordance with the invention inserted therein.
Figure 11:
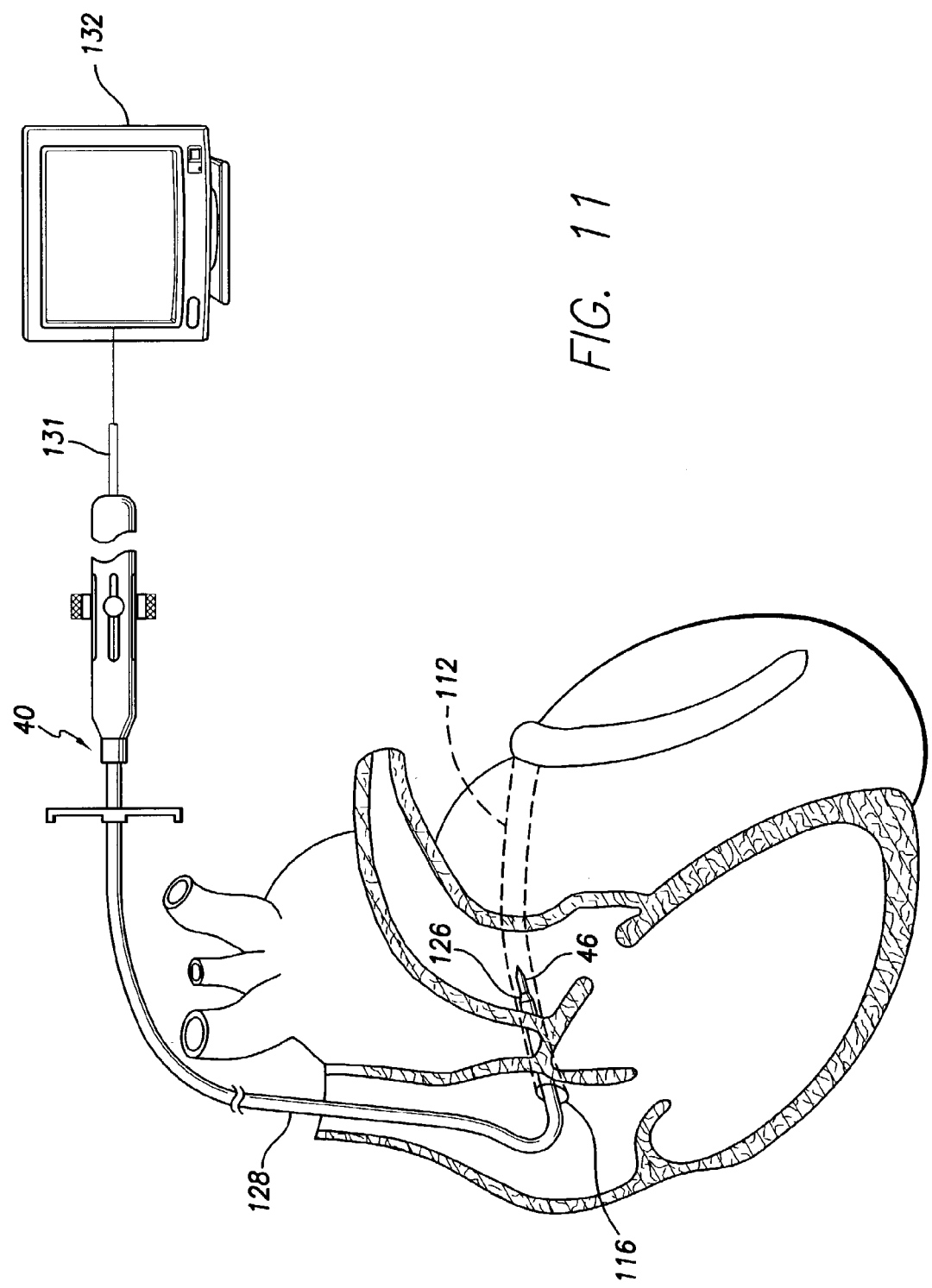
FIG. 11 is a perspective view of the anterior portion of the heart showing the introducer sheath and steerable obturator combination of FIG. 10 delivered with the aid of the steerable obturator into the coronary sinus through the coronary sinus os.

As illustrated in FIG. 9, the distal, tapered end 126 of an introducer sheath 128 having a dilator 130 fully inserted therein has been placed, in the manner already described, in the right atrium 114 near the coronary sinus OS 116. With reference to FIGS. 10 and 11, after removal of the dilator from the introducer sheath, an obturator 40 in accordance with the invention and specifically in accordance with the embodiments of FIGS. 3–8, is inserted into the sheath 128 and advanced therein until at least a portion of the flexible distal end section 46 projects from the distal end 126 of the sheath. Using the knobs 92–95 to deflect the distal end section 46 of the obturator body as required, the distal end of the sheath is maneuvered through the coronary sinus os and into the coronary sinus. Fluoroscopy may be used in aid of the delivery of the distal end of the sheath through the coronary sinus os and into the coronary sinus in which case contrast fluid may be injected into the right atrium via the conduit in the obturator actuator and central lumen of the obturator body. Alternatively, echocardiography employing an intravascular ultrasound transducer or an array of transducers on the distal end of an elongated member 131 connected to a monitor 132 and passed through the central lumen of the obturator 40 allows the two dimensional visualization of coronary structures such as the coronary sinus os to aid the steering of the introducer sheath by means of the steerable obturator through the coronary sinus os and into the coronary sinus without fluoroscopic guidance and the attendant need for a high level of operator skill. Available scanning depths of several millimeters provide adequate spatial resolution for this purpose. As a further alternative, optical imaging employing an optical fiber bundle comprising light emitting and receiving fibers passed through the obturator and connected to a monitor may be employed. This technique uses near infrared radiation at a wavelength where absorptance and scattering by blood cells is minimized to provide good image resolution at depths of up to about 1 cm. The central passage defined by the obturator comprising the lumens 56 and 86 may also be used for the introduction of drugs or therapeutic agents into the heart.

Figure 12:
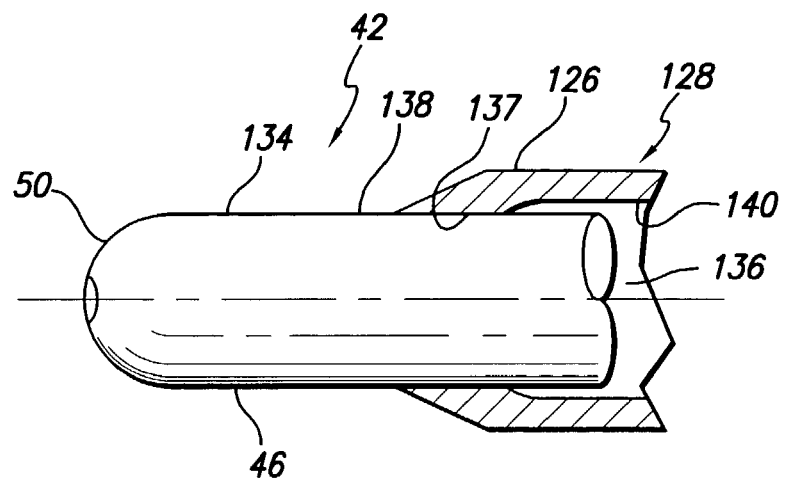
FIG. 12 is an enlarged side view, partly in section, of the distal end of the introducer sheath showing the tip of the steerable obturator of the invention projecting therefrom.

As seen in FIG. 12, the flexible distal end section 46 of the obturator body 42 has an outer, generally cylindrical surface 134. The introducer sheath 128 has an internal lumen 136 a section 137 of which extends proximally from a distal edge 138 on the distal extremity of the tapered distal end 126 of the sheath 128. Proximally of the lumen section 137, the lumen 136 expands to a larger diameter portion 140 to provide adequate clearance around the outer surface 134 of the distal end 46 of the obturator body along substantially the entire remaining length of the introducer sheath. The dimensional relationship (explained in greater detail in the description of FIG. 13, below) between the outer surface 134 of the obturator's distal end 46 and the cylindrical lumen section 137 provides for a close but freely slidable fit between these elements. In this fashion, as seen in the detail of FIG. 12, the distal edge 138 on the tapered distal end 126 of the introducer sheath lies against the outer surface 134 of the flexible distal tip section 46 of the obturator body 42 so as to minimize protrusion of the edge 138 and present to the body tissue a substantially smooth, continuous surface. Accordingly, the edge 138 is not disposed to engage cardiac tissue as the distal end 126 of the introducer sheath is maneuvered into the coronary sinus by means of the steerable obturator.

Figure 13:
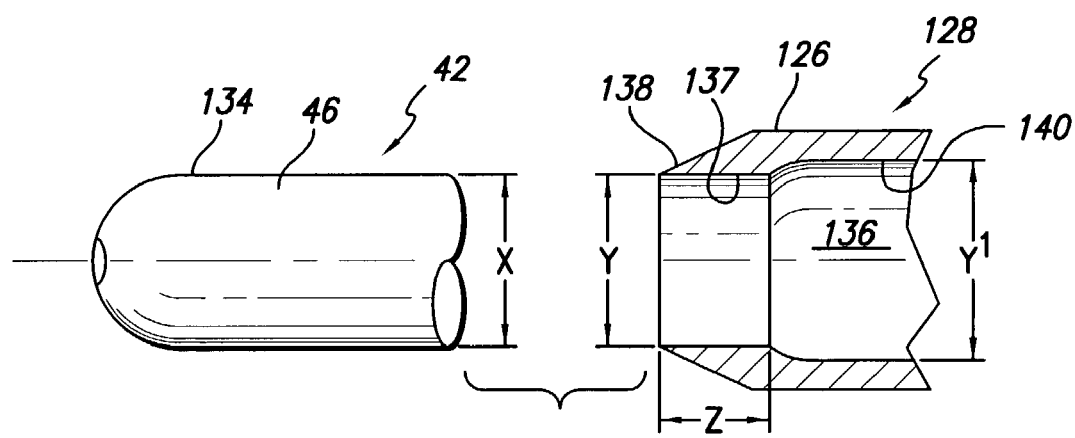
FIG. 13 is an enlarged side view, partly in section, of the distal ends of the introducer sheath and obturator of FIG. 12 showing the dimensional relationships between those elements.

With reference to the detail of FIG. 13, the outer surface 134 of the flexible distal end 46 of the obturator body 42 has a diameter, x; the section 137 of the introducer sheath lumen has a diameter y and a length z, and the main, expanded portion 140 of the introducer sheath lumen 136 has a diameter y'. By way of example and not by way of limitation, x=8 to 9 F (0.104 to 0.117 inch) and y=(x−0.001) to (x+0.002) inch. Accordingly, the dimensional relationship between the elements 46 and 137 is such so as to range from a slightly interfering fit to a small clearance fit. The objective is a "line-to-line" fit, that is, a fit that has neither interference nor clearance. Further, in this example, z may be 1 mm and y' may be (y+0.002) inch.

Figure 14:
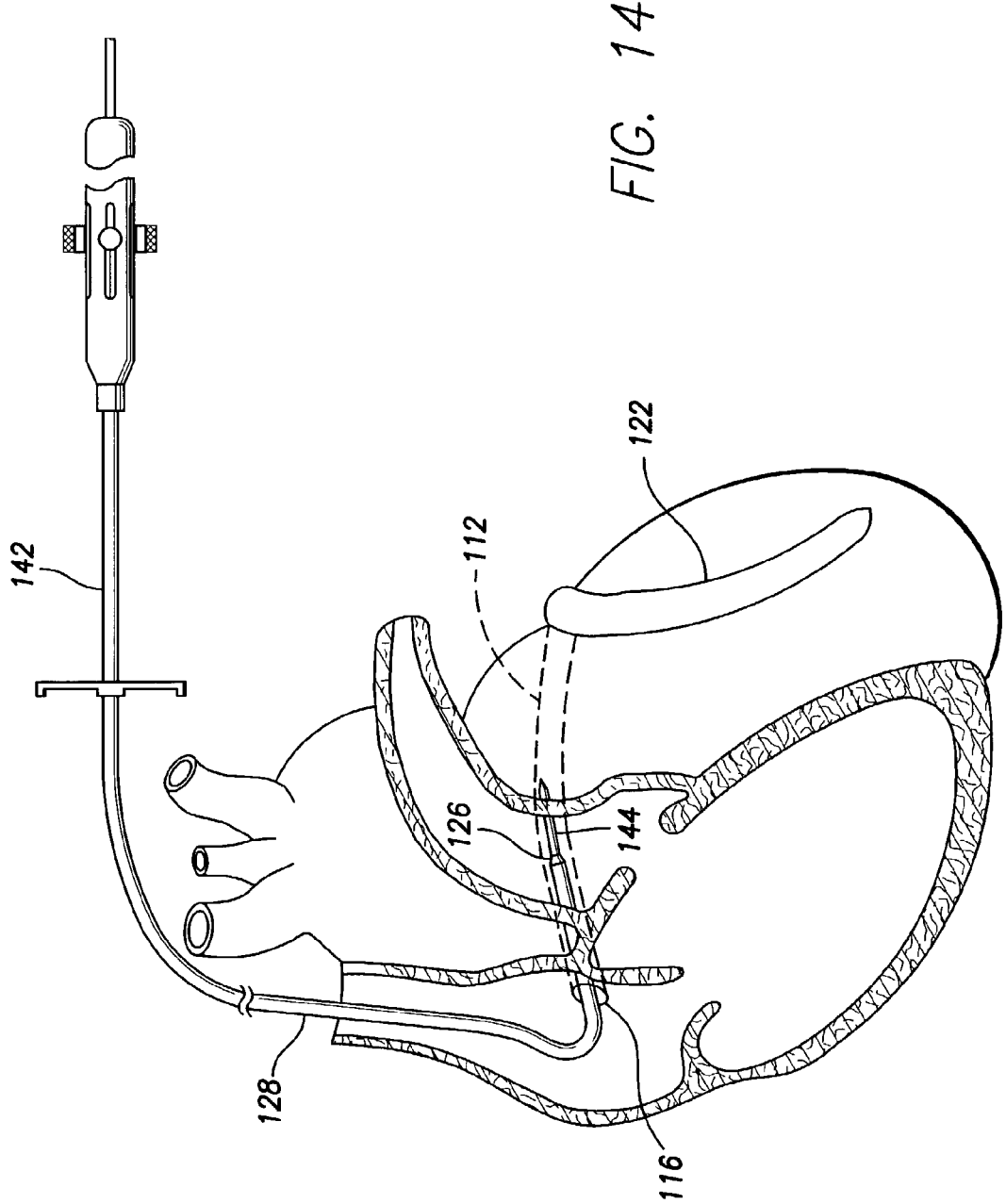
FIG. 14 is a perspective view of the anterior portion of the heart after withdrawal of the obturator from the introducer sheath and insertion of an implantable lead in the sheath.

FIG. 14 shows the distal end 126 of the introducer sheath having passed through the coronary sinus os 116 and penetrating the coronary sinus 112 under the guidance afforded by the steerable obturator 40. The obturator is then withdrawn from the sheath. With reference to FIG. 14, a lead 142 is then passed through the central lumen of the sheath and advanced so that the distal end portion 144 of the lead is within the coronary sinus. The central lumen of the introducer sheath may also serve as a conduit for the infusion of appropriate drugs or therapeutic agents.

Figure 15:
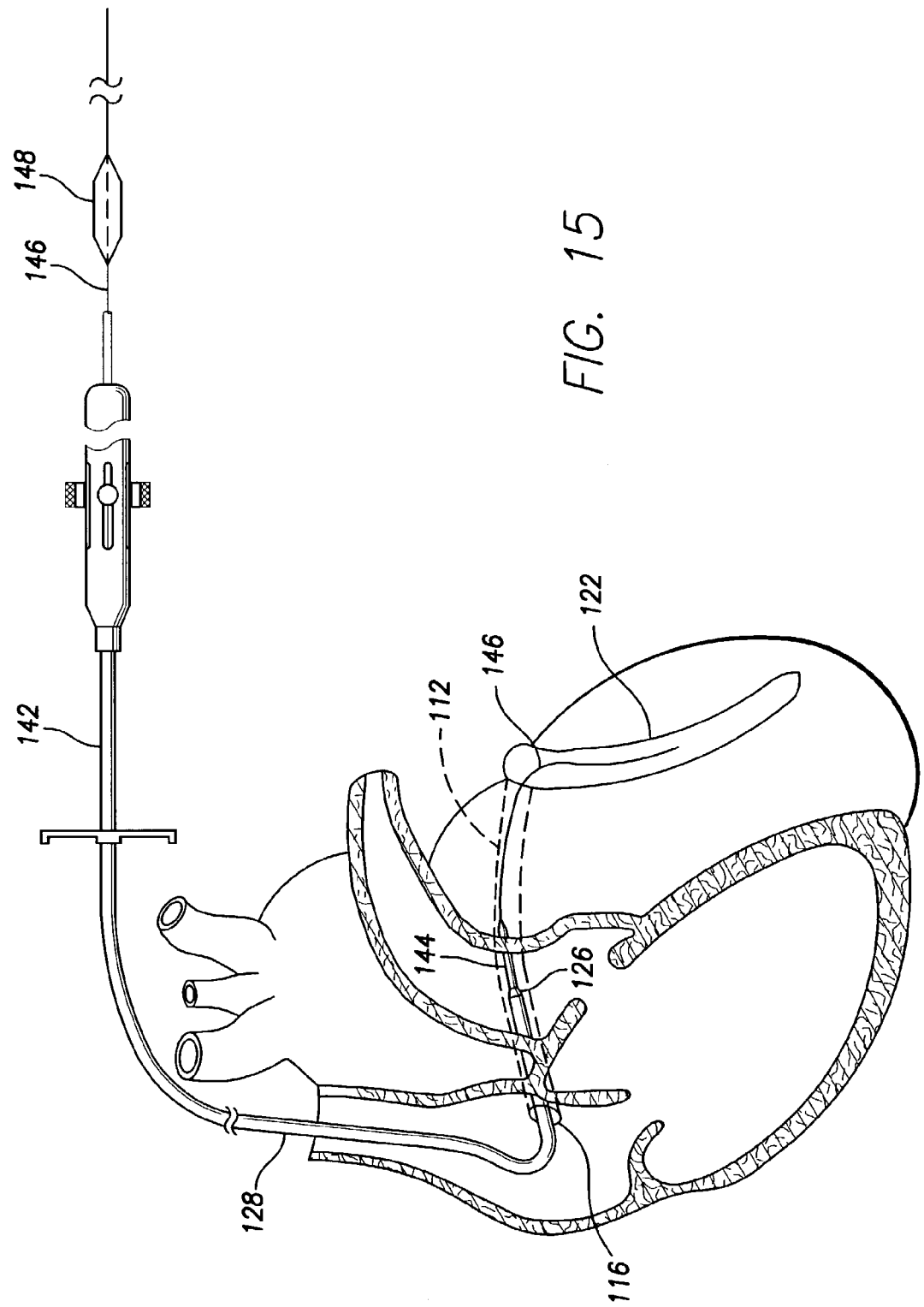
FIG. 15 is a perspective view of the anterior portion of the heart showing a guide wire passed through the lead and advanced through the coronary sinus and into a target vessel overlying the left side of the heart.
Figure 16:
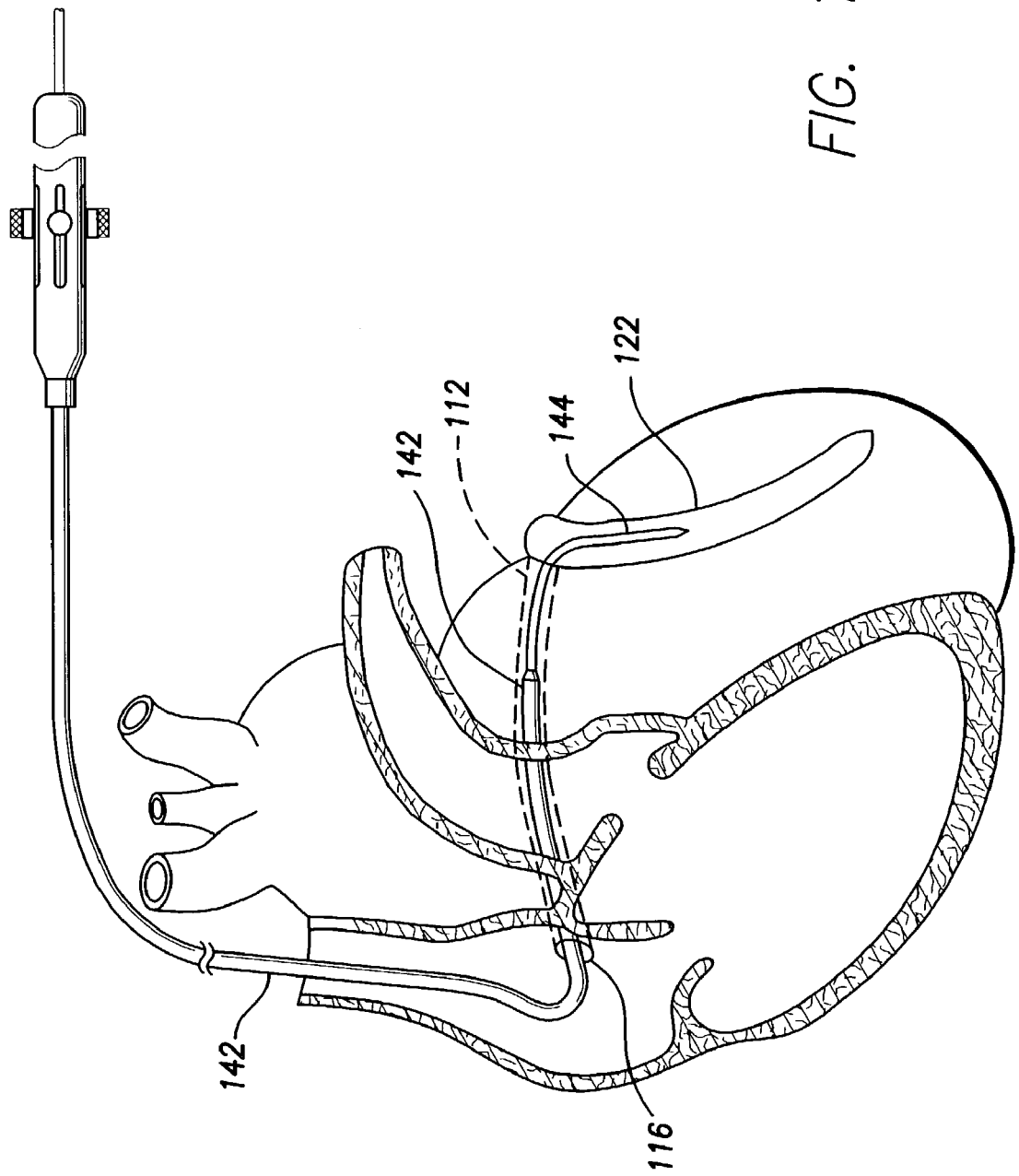
FIG. 16 is a perspective view of the anterior portion of the heart showing the lead after its delivery "over the wire" to its destination in a target vessel and after withdrawal of the introducer sheath and the guide wire.

FIG. 15 shows the use of a guide wire 146 passed through the lead, for placement of the distal portion 144 of the lead 142 within a target left side vessel. The distal end of the guide wire is moved into a target vessel such as the LPV vein 122. In this fashion, the lead may be moved along the guide wire to its final destination (FIG. 16) in accordance with "over-the-wire" implantation techniques well known in the art.

The guide wire 146 is steered using a releasable or selectively lockable clamp 148 carried by the guide wire. When loosened, the clamp can be slid along the guide wire and re-tightened in a new position as the guide wire is advanced. Torque applied to the tightened clamp rotates the guide wire as it is advanced to maneuver the flexible end of the guide wire into a target vessel of the heart. After the lead is advanced over the wire into the vessel, and is in place therein, the guide wire is withdrawn.

FIG. 17 shows a specific, exemplary form of an obturator 150 in accordance with another embodiment of the invention which eliminates the need for actuating members in the form of wires or cables and related elements. The obturator 150 includes an obturator body 152 having a flexible, distal end section 154 terminating at a tip 156 having an outer rounded surface 158. A handle 160 is attached to the proximal end of the obturator body 152. The obturator includes a central, longitudinal lumen 162 extending the length of the obturator for receiving an actuator 164 for deflecting the flexible distal end section 154. With reference to FIG. 18, the actuator 164 of the second embodiment is in the form of a stylet 166 having a pre-curved distal end 168, for example, in the form of a J-shape, and a proximal end carrying a torque knob 170. When the stylet 166 is fully inserted in the obturator 150 as shown in FIG. 19, the pre-curved distal end 168 deflects the flexible distal end section 154 of the obturator body so as to provide appropriate steerability. Rotation of the stylet 166 by means of the knob 170 determines the angular direction of the deflection of the tip section 154 as required to cannulate the coronary sinus.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. An omnidirectionally steerable obturator to facilitate the delivery of the distal tip of an introducer sheath into the coronary sinus of a heart, the steerable obturator comprising:
an obturator body extending longitudinally along a central axis, the obturator body being configured to be received by the introducer sheath, the obturator body having a flexible, deflectable distal end section terminating in a rounded distal tip; and
an actuator controllable from a proximal end of the obturator body, the actuator being operatively associated with the flexible distal end section of the obturator body to cause deflection of the flexible distal end section of the obturator body to cause deflection to the flexible distal end section of the obturator body to facilitate passage of the distal end section of the obturator body and the distal tip of the introducer sheath into the coronary sinus of the heart;
the actuator comprises a control handle attached to the proximal end of the obturator body;
the obturator body further includes a first set of parallel, longitudinally extending, off axis lumens that are diametrically opposing and a second set of parallel, longitudinally extending, off axis lumens that are diametrically opposing;
the control handle includes a first set of manually movable control members and a second set of manually movable control members, each of the movable control members longitudinally and slidingly retractable along the control handle and longitudinally and slidingly advanceable along the control handle; and
a cable contained within each off-axis lumen, each cable having a distal end anchored to an interior surface of the distal end section at an off-axis point and a proximal end mechanically coupled to one of the movable control members on the control handle;
wherein the first set of movable control members is effective to steer the distal end section in a first plane and the second set of movable control members is effective to steer the distal end section in a second plane;
wherein the first plane is substantially transverse to the second plane; and
wherein each of the movable control members is independently advanced or retracted in coordination with the other movable control members to deflect the distal end section to guide and steer the distal tip of the obturator.

2. The obturator of claim 1 in which:
the obturator body is configured to be received in a close fit within at least the tip of the introducer sheath.

3. The obturator of claim 1 in which:
the distal ends of the cables are anchored along a plane transverse of the central axis.

4. The obturator of claim 1 further comprising:
a central, longitudinal lumen extending the length of the obturator providing a passage for an object such as a guide wire, a stylet, a diagnostic device and/or an imaging probe, or for the infusion of a drug or other therapeutic agent.

5. The obturator of claim 1 in which:
the distal end of the cable is directly anchored to the interior surface of the distal end section, and the proximal end of the cable is directly attached to one of the movable control members.

6. The obturator of claim 1 in which:
the longitudinal retraction at a distance x of the movable control member causes the proximal end of the cable to retract the same distance x, and a longitudinal advancement at a distance y of the movable control member causes the proximal end of the cable to advance the same distance y.

7. The obturator of claim 1 in which:
the distal ends of the actuating members are anchored at points spaced apart along the length of the obturator body.

8. The obturator of claim 1 in which:
the distal end of at least one of the actuating members is anchored at a point along the length of the obturator body and the distal ends of the remaining actuating members are anchored along a plane transverse of the central axis, the plane being longitudinally spaced apart from said first-mentioned anchor point.

9. The obturator of claim 1 in which:
the actuator comprises a stylet adapted to be received within a longitudinally-extending lumen formed in the obturator body, the stylet having a pre-curved, flexible distal tip section.

10. The obturator of claim 9 in which:
the pre-curved, flexible distal tip section of the stylet has a generally J-shape.

11. An apparatus to facilitate the delivery of a transvenous implantable lead into the coronary sinus of a heart, the apparatus comprising:
an introducer sheath having a central, longitudinally-extending lumen and a distal end tapered to an edge at a distal extremity of the sheath; and
an elongated obturator comprising:
a steerable distal end configured to be received in a close fit within a portion of the lumen of the introducer sheath within the distal end of the sheath, the obturator having a length relative to that of the introducer sheath so that the steerable distal end of the obturator projects distally from the distal extremity of the introducer sheath when fully inserted therein;
an obturator body extending longitudinally along a central axis, the obturator body having a first set of parallel, longitudinally extending, off axis lumens that are diametrically opposing and a second set of parallel, longitudinally extending, off axis lumens that are diametrically opposing;
an actuator having a control handle attached to a proximal end of the obturator body, the control handle having a first set of parallel, longitudinally extending, off axis lumens that are diametrically opposing and a second set of parallel, longitudinally extending, off axis lumens that are diametrically opposing; and
a cable contained within each off-axis lumen, each cable having a distal end anchored to an interior surface of the steerable distal end at an off-axis point and a proximal end mechanically coupled to one of the movable control members on the control handle;
wherein the first set of movable control members is effective to steer the distal end in a first plane and the second set of movable control members is effective to steer the distal end in a second plane;
wherein the first plane is substantially transverse to the second plane; and
wherein each of the movable control members is independently advanced or retracted in coordination with the other movable control members to deflect the distal end to guide and steer the obturator.

12. The obturator of claim 11 in which:

the distal end of the obturator has an outer surface; and said edge at the distal extremity of the sheath lies against said outer surface when the distal end of the obturator projects from the distal extremity of the sheath.

13. The obturator of claim 11 in which:

the steerable distal end of the obturator is flexible and deflectable.

14. The obturator of claim 13 in which:

the actuator comprises a stylet having a pre-curved flexible tip section adapted to be received by a central lumen of the obturator, the stylet having a length so that when fully inserted within the obturator, the pre-curved tip section resides in and tends to deflect the flexible distal section of the obturator body, rotation of the stylet deflecting said distal end section of the obturator body in a selected direction whereby the passage of the obturator and the distal end of the introducer sheath carried thereby through the coronary sinus os and into the coronary sinus of the heart is facilitated.

15. The obturator of claim 14 in which:

the pre-curved, flexible distal tip section of the stylet has a generally J-shape.

16. The obturator of claim 11 further comprising:

a central, longitudinal lumen extending the length of the obturator providing a passage for an object such as a guide wire, a stylet, a diagnostic device and/or an imaging probe, or for the infusion of a drug or other therapeutic agent.

17. The obturator of claim 11 in which:

the distal end of the cable is directly anchored to the interior surface of the steerable distal end, and the proximal end of the cable is directly attached to one of the movable control members.

18. The obturator of claim 11 in which:

the longitudinal retraction at a distance x of the movable control member causes the proximal end of the cable to retract the same distance x, and a longitudinal advancement at a distance y of the movable control member causes the proximal end of the cable to advance the same distance y.

* * * * *